United States Patent [19]

Chmel

[11] Patent Number: 5,203,700
[45] Date of Patent: Apr. 20, 1993

[54] PHYSICAL LOCK OF GASKETS SURROUNDING NATURAL TEETH

[76] Inventor: James M. Chmel, 3050 Riverview Dr., Eau Claire, Wis. 54703

[21] Appl. No.: 800,959

[22] Filed: Dec. 2, 1991

[51] Int. Cl.$^5$ .................. A61C 13/12; A61C 13/225
[52] U.S. Cl. ...................................... 433/169; 433/172
[58] Field of Search .................... 433/167, 168.1, 169, 433/171, 172, 177

[56] References Cited

U.S. PATENT DOCUMENTS

| 3,716,918 | 2/1973 | Tole et al. | 433/172 |
| 4,634,381 | 1/1987 | Kusano et al. | 433/172 |
| 4,681,542 | 7/1987 | Baum | 433/172 |
| 4,764,115 | 8/1988 | Willits et al. | 433/177 |
| 5,098,295 | 3/1992 | Durr et al. | 433/172 |

*Primary Examiner*—Gene Mancene
*Assistant Examiner*—Cindy A. Cherichetti
*Attorney, Agent, or Firm*—Palmatier, Sjoquist & Helget

[57] ABSTRACT

As known, comfortable, yieldable elastomeric gasket liners are used to couple a prosthetic denture to an individual's natural tooth. The gasket liners are generally affixed to the prosthetic denture by chemical bonding agents. The gasket liners are exposed to shearing and separating forces whenever the prosthetic denture is withdrawn or inserted into position for use. As known, the bonding agents fail to adequately maintain contact between the yieldable elastomeric gasket liners and a prosthetic denture. Repair or replacement of a gasket liner is thereby required, necessitating loss of use and repair. The invention relates to an improved prosthetic denture for mechanically and physically locking a yieldable elastomeric gasket liner to the interior aperture walls of the prosthetic denture. The invention includes a prosthetic denture having grooves which encircle the interior surfaces surrounding an aperture of a prosthetic denture. The grooves provide a mechanical locking mechanism which in conjunction with a chemical bonding agent, deters separation between a gasket liner and the interior aperture walls of a prosthetic denture during removal from and insertion of the denture into a mouth.

11 Claims, 1 Drawing Sheet

PHYSICAL LOCK OF GASKETS SURROUNDING NATURAL TEETH

BACKGROUND OF THE INVENTION

As known, individuals use prosthetic denture apparatus in order to overcome various natural oral deficiencies. Many prosthetic denture apparatus include apertures in the denture for engagement and coupling with remaining natural teeth. A yieldable elastomeric gasket liner inserted into a prosthetic denture apparatus creates a seal between the denture and the natural teeth. The yieldable elastomeric gasket liner also provides comfort to an individual during the use of the denture. Generally the yieldable elastomeric gasket liner is formed of silicon, silicon rubber, or an elastic-type material.

As known, a yieldable elastomeric gasket liner is generally affixed to a prosthetic denture apparatus by use of a chemical bonding agent.

Upon the completion of use of a prosthetic denture apparatus, an individual will generally remove the denture. Normal termination of use occurs during sleep periods or when an individual desires to clean the denture. Repeated insertion and removal of a prosthetic denture apparatus exposes the yieldable elastomeric gasket liner to various shearing forces with respect to the chemical bond affixing the gasket to a denture. Continued exposure of the gasket to these shearing forces results in the separation of the gasket from the prosthetic denture apparatus. A prosthetic denture apparatus becomes uncomfortable for additional use necessitating repairs when separation of the gasket from the denture occurs.

The present invention improves a prosthetic denture apparatus providing a mechanical and physical lock between a yieldable elastomeric gasket liner and a prosthetic denture. The present invention operates in conjunction with a chemical bonding agent to minimize resulting separation caused by repeated exposure of the yieldable elastomeric gasket liner to shearing forces which occur by insertion and removal of a denture from a mouth. The invention enhances the usefulness and life expectancy of the yieldable elastomeric gasket liner and/or denture used by an individual.

SUMMARY OF THE INVENTION

The present invention relates to an improved prosthetic denture which mechanically and chemically bonds to a yieldable elastomeric gasket liner for use in an individual's mouth.

An object of the invention is to provide an improved prosthetic denture which reduces the shearing, separation, and/or tearing of the yieldable elastomeric gasket liner from engagement with the denture, during repeated insertion into and removal of the denture from an individual's mouth.

Another object of the invention is the provision of a new and improved prosthetic denture of relatively simple and inexpensive construction and operation which is safe, durable, comfortable, and which mechanically assists a chemical bonding agent to maintain engagement between a yieldable elastomeric gasket liner and the interior of the prosthetic denture, without fear of damage to the denture, yieldable gasket liner, and/or injury to persons.

A feature of the invention includes semicircular grooves fashioned into the interior walls of a prosthetic denture.

Another feature of the invention is the location of the semicircular grooves which surround apertures which traverse a prosthetic denture.

Still another feature of the invention is the mechanical interaction of the grooves with a yieldable elastomeric gasket liner.

Still another feature of the invention is the interaction between the grooves, a chemical bonding agent, and a yieldable gasket liner which minimizes shearing, separation, and/or tearing of the gasket liner from attachment to the prosthetic denture, upon insertion into and withdrawal from an individual's mouth.

DETAILED DESCRIPTION OF THE PREFERRED EMBODIMENTS

One form of the invention is illustrated and described herein. The prosthetic denture apparatus is indicated in general by the numeral 10. The denture 10 is preferably used with a yieldable elastomeric gasket liner indicated in general by the numeral 14.

Figure 1:
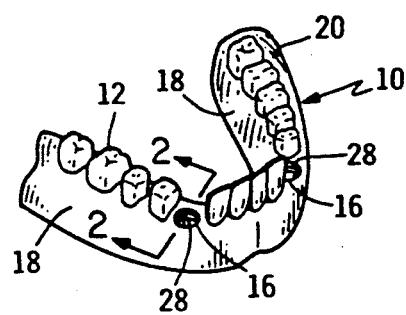
FIG. 1 is an isometric view of the invention.

As seen in FIG. 1, the prosthetic denture apparatus 10 consists of a plurality of extending or depending prosthetic teeth 12, which in all respects simulate and resemble the corresponding natural teeth of an individual. The denture 10 also includes one or a plurality of apertures 16 suitably adapted for engagement with the yieldable elastomeric gasket liner 14 for coupling the denture 10 to a natural tooth 8. The denture 10 also includes a pair of walls 18 and a plate portion 20. The walls 18 contain interior and exterior surfaces 22 and 24 respectively. The plate portion 20 suitably extends between the walls 18 proximal to the prosthetic teeth 12. The exterior surfaces 24 of the walls 18 are preferably tapered and formed in all respects to simulate and resemble a natural gum of an individual's mouth. The interior surfaces 22 of the walls 18 are preferably formed and tapered for suitable engagement with the yieldable elastomeric gasket liner 14 to provide comfort to a person during use of the denture 10. The denture 10, walls 18, plate portion 20, and apertures 16 may be suitably formed by molding, milling, and/or drilling as known in the art. The denture 10, walls 18, plate portion 20, and prosthetic teeth 12 are preferably formed of acrylic or plastic material as known in the art.

The apertures 16 traverse the plate portion 20 forming openings suitably adapted for receipt of natural teeth 8. Generally, the apertures 16 are oversized and are formed for engagement to the gasket liner 14.

The yieldable elastomeric gasket liner 14 is preferably formed of silicon, silicon rubber and/or other elastic-type material. The yieldable elastomeric gasket liner 14 generally remains affixed to the interior surfaces 22 of the walls 18 and the plate portion 20. The yieldable elastomeric gasket liner 14 is generally formed to consistently and naturally engage the natural tooth of an individual. During use the yieldable elastomeric gasket liner 14 functions to provide a seal between an individual's natural tooth and a prosthetic denture apparatus 10, thereby, preventing air and/or food particles or other substances from becoming trapped under the denture 10 between a person's gums and the yieldable elastomeric gasket liner 14. The yieldable elastomeric gasket liner 14 also functions as a cushion, thereby, providing comfort to an individual during use of the denture apparatus 10. The yieldable elastomeric gasket liner 14 also remains suitably affixed to the apertures 16 maintaining a seal between a natural tooth 8 and the denture 10.

Grooves 28 are preferably milled into the interior surfaces 22 of the walls 18 completely surrounding the apertures 16. The grooves 28 are generally circular and remain as large as space will permit around an aperture 16. The grooves 28 may also be suitably formed into the interior surfaces 22 by molding, cutting, sculpting, tooling, carving, engraving, casting and/or etching.

The indentation of the grooves 28 are generally semicircular in shape. However, the indentation of the grooves 28 may also be suitably rectangular, square, and/or V-shaped.

The grooves 28 generally encircle the aperture 16. The grooves 28 are preferably horizontal with respect to the aperture opening 16. The grooves 28 may suitably remain horizontal and parallel to the plate portion 20. A single groove 28 or a plurality of grooves 28 may suitably surround the aperture 16.

The grooves 28 do not penetrate or breach the integrity of the exterior surface 24 of the denture apparatus 10. The grooves 28 do not adversely effect the strength of the walls 18 of the denture apparatus 10. The grooves 28 are preferably located below the plate portion 20, surrounding an aperture 16, along the interior surfaces 22 of the walls 18. The grooves 28 provide for mechanical engagement, in conjunction with chemical bonding, affixing the yieldable elastomeric gasket liner 14 to the interior surfaces 22 of the denture apparatus 10.

As previously known in the art the yieldable elastomeric gasket liner 14 was affixed to the interior surfaces of a denture apparatus 10 only through chemical bonding, via the mechanism of a bonding agent. As known, chemical bonding failed to adequately fix the yieldable elastomeric gasket liner 14 to a denture apparatus 10 over an extended period of time. The gasket liners frequently separated or tore from the denture 10 when exposed to binding, shearing, and/or stress forces along the main axis of an aperture 16. The binding or stress forces would occur as a result of friction between the gasket liner 14 and a natural tooth 8 upon insertion or removal of the denture 10 from a mouth. As known, elimination of binding, stress and friction forces is not possible due to the necessity of the preferred airtight seal between a natural tooth and the gasket liner 14. In addition, friction and wear to a natural tooth 8 are minimized by engagement between the gasket liner 14 and a natural tooth 8, as opposed to contact between a tooth 8 and a denture 10.

Figure 2:
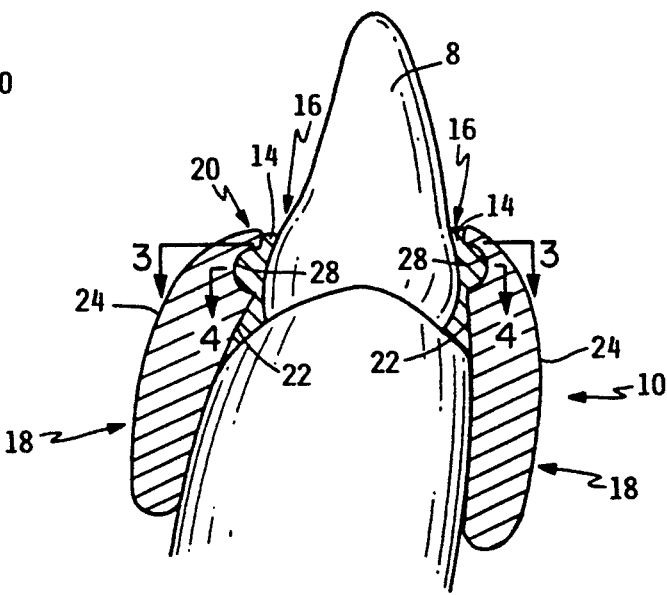
FIG. 2 is a cross-sectional side view taken along the line 2—2 of FIG. 1, with the invention in operable position.
Figure 3:
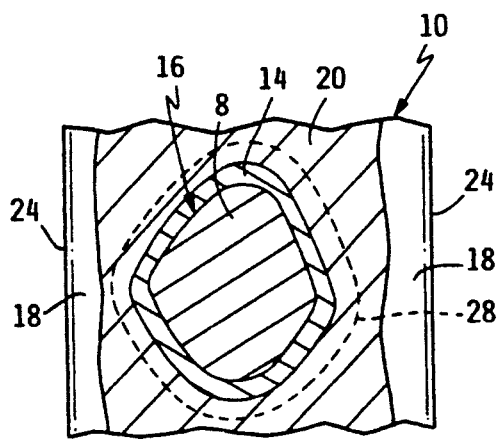
FIG. 3 is a cross-sectional top view taken along the line 3—3 of FIG. 2.
Figure 4:
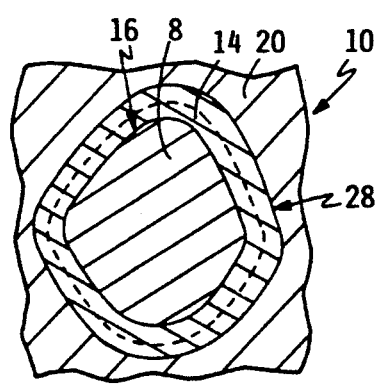
FIG. 4 is a cross-sectional top view taken along the line 4—4 of FIG. 2.

The grooves 28 in conjunction with chemical bonding to the liner 14, as known as seen in FIGS. 2 and 3, provide a denture apparatus 10 with a mechanical locking mechanism maintaining contact between the yieldable elastomeric gasket liner 14 and the interior surfaces 22 of the denture apparatus 10. The chemical bonding agent may be selected from the group of chemical bonding agents which are suitable for use with prosthetic dentures. The existence of mechanical support as provided by the grooves 28 significantly enhance the strength of the engagement between the gasket liner 14 and the interior surfaces 22 of the denture 10. The mechanical support provided by the grooves 28 significantly increases the useful life expectancy of a denture apparatus 10. The mechanical support provided by the grooves 28 minimizes separation, shearing, and/or tearing of the yieldable elastomeric gasket liner 14 from the interior surfaces 22 which result upon exposure of the gasket liner 14 to shearing forces which occur during insertion into and removal of the denture apparatus 10 from a mouth.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An improved prosthetic denture apparatus adapted for engagement to natural teeth, said denture apparatus having an interior and a plurality of apertures comprising:
   a) interior walls for each aperture;
   b) a continuous groove located in each of said interior walls about said aperture; and
   c) a gasket liner affixed to said interior of said denture and said interior walls and filling said grooves, said gasket liner forming a reduced size opening for engagement to said natural teeth.

2. The prosthetic denture apparatus of claim 1, wherein the interior walls for each aperture have a plurality of grooves.

3. The prosthetic denture apparatus of claim 2, wherein said grooves extend substantially horizontally along said interior walls to encircle said aperture.

4. The prosthetic denture apparatus of claim 1, wherein said grooves are of a substantially semicircular cross-sectional shape adapted to surround said apertures in said denture.

5. The prosthetic denture apparatus of claim 1, wherein said gasket liner is formed of an elastic-type material.

6. The prosthetic denture apparatus of claim 1, further comprising a chemical bonding agent affixing said gasket liner to said interior of said denture and said interior walls and said grooves.

7. An improved prosthetic denture apparatus adapted for engagement to natural teeth comprising:
   a) a pair of opposite walls, each wall having exterior and interior surfaces and upper and lower portions;
   b) a plate bridging between said upper portions of said opposite walls;
   c) at least one tooth-receiving aperture through said plate, said apertures having interior surfaces of predetermined and finite depths;
   d) at least one groove along said interior surface of said apertures; and
   e) a gasket liner affixed in engagement with said interior surfaces of said walls, and interior surfaces of said apertures, and filling said at least one groove said gasket liner further adapted for engagement to said natural teeth.

8. The prosthetic denture apparatus of claim 7, wherein said grooves extend horizontally along said interior surface of said apertures.

9. The prosthetic denture apparatus of claim 7, wherein said grooves are of a semicircular cross-sectional shape adapted to encircle said aperture in said denture.

10. The prosthetic denture apparatus of claim 7, wherein said gasket liner is formed of an elastic-type material.

11. The prosthetic denture apparatus of claim 7, further comprising a chemical bonding agent affixing said gasket liner to said interior surfaces of said walls and said interior surfaces of said aperture and said grooves.

* * * * *